(12) United States Patent
Dakka et al.

(10) Patent No.: US 9,963,403 B2
(45) Date of Patent: May 8, 2018

(54) PROCESS AND APPARATUS FOR THE CONVERSION OF HYDROCARBONS

(71) Applicant: ExxonMobil Chemical Patents Inc., Baytown, TX (US)

(72) Inventors: Jihad M Dakka, Whitehouse Station, NJ (US); Robert G. Tinger, Friendswood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days. days.

(21) Appl. No.: 14/872,388

(22) Filed: Oct. 1, 2015

(65) Prior Publication Data

US 2016/0115094 A1 Apr. 28, 2016

Related U.S. Application Data

(60) Provisional application No. 62/069,049, filed on Oct. 27, 2014.

(51) Int. Cl.
| | | |
|---|---|---|
| *C07C 2/86* | (2006.01) |
| *C07C 45/00* | (2006.01) |
| *C07C 5/27* | (2006.01) |
| *C07C 51/265* | (2006.01) |
| *C07C 7/12* | (2006.01) |
| *C07C 7/163* | (2006.01) |

(52) U.S. Cl.
CPC .............. *C07C 2/864* (2013.01); *C07C 2/865* (2013.01); *C07C 5/2702* (2013.01); *C07C 5/2732* (2013.01); *C07C 7/12* (2013.01); *C07C 7/163* (2013.01); *C07C 45/006* (2013.01); *C07C 51/265* (2013.01)

(58) Field of Classification Search
CPC ....... C07C 2/864; C07C 2/865; C07C 5/2732; C07C 51/265; C07C 7/12; C07C 7/163; C07C 45/006; C07C 5/2702
See application file for complete search history.

(56) References Cited

U.S. PATENT DOCUMENTS

| | | | | |
|---|---|---|---|---|
| 2,552,268 A | * | 5/1951 | Emerson ............... | C07C 51/265 502/150 |
| 3,686,343 A | * | 8/1972 | Bearden, Jr. .......... | B01J 20/186 208/310 R |
| 3,702,886 A | | 11/1972 | Argauer et al. | |
| 3,709,979 A | | 1/1973 | Chu | |
| 3,832,449 A | | 8/1974 | Rosinski et al. | |
| 3,965,207 A | | 6/1976 | Weinstein | |
| 4,016,218 A | | 4/1977 | Haag et al. | |
| 4,016,245 A | | 4/1977 | Plank et al. | |
| 4,076,842 A | | 2/1978 | Plank et al. | |
| 4,255,606 A | * | 3/1981 | Tse ....................... | C07C 5/2724 585/477 |
| 4,300,014 A | | 11/1981 | Yamasaki et al. | |
| 4,356,338 A | | 10/1982 | Young | |
| 4,375,573 A | | 3/1983 | Young | |
| 4,377,718 A | * | 3/1983 | Sato ..................... | C07C 2/864 585/467 |
| 4,670,616 A | | 6/1987 | De Simone et al. | |
| 5,110,776 A | | 5/1992 | Chitnis et al. | |
| 5,231,064 A | | 7/1993 | Absil et al. | |
| 5,348,643 A | | 9/1994 | Absil et al. | |
| 7,453,018 B2 | | 11/2008 | Dakka et al. | |
| 8,252,967 B2 | | 8/2012 | Hagemeister et al. | |
| 8,502,008 B2 | | 8/2013 | Kinn et al. | |
| 8,507,744 B2 | | 8/2013 | Hagemeister et al. | |
| 8,529,757 B2 | | 9/2013 | Go et al. | |
| 8,541,639 B2 | | 9/2013 | Ou et al. | |
| 8,569,559 B2 | | 10/2013 | Ou | |
| 8,692,044 B2 | | 4/2014 | Ou et al. | |
| 8,697,929 B2 | | 4/2014 | Ou et al. | |
| 8,716,541 B2 | | 5/2014 | Ou | |

(Continued)

FOREIGN PATENT DOCUMENTS

| | | |
|---|---|---|
| JP | 58-164527 A | 3/1982 |
| WO | 00/40527 A1 | 7/2000 |
| WO | 2012/074613 A1 | 6/2012 |
| WO | 2012/134552 A1 | 10/2012 |
| WO | WO2013/180888 | * 12/2013 |

OTHER PUBLICATIONS

"Group Notation Revised in Periodic Table," Chemical and Engineering News, 1985, vol. 63, No. 5, p. 27.
Wang, Yong et al., "Highly Selective Hydrogenation of Phenol and Derivatives Over a Pd Carbon Nitride Catalyst in Aqueous Media," Journal of the American Chemical Society, 2011, vol. 133, pp. 2362-2365.
Liu, Huizhen et al., "Selective Phenol Hydrogenation to Cyclohexanone Over a Dual Supported Pd-Lewis Acid Catalyst," Science, 2009, vol. 326, pp. 1250-1252.
Dimian, A.C. et al., "Chemical Process Design, Computer-Aided Case Studies," 2008, Wiley-VCH Verlag GmbH & Co. KGaA.
Kirk-Othmer, "Encyclopedia of Chemical Technology," 1979, Third Edition, vol. 7, pp. 410-416.

(Continued)

*Primary Examiner* — Pancham Bakshi
*Assistant Examiner* — Mark R Luderer

(57) ABSTRACT

A hydrocarbon conversion process is described. The process includes contacting in a reactor an inert gas with one or more catalyst compositions suitable for methylation of toluene and hydrogenation of phenol; contacting a reducing agent with the one or more catalyst compositions under conditions suitable for reducing metal oxide content of the catalyst composition; contacting at least part of toluene and/or benzene-containing with a oxygenate in the presence of the one or more catalyst compositions and under conditions effective to convert toluene to xylenes and produce a reactor effluent stream comprising para-xylene and having a lower concentration of phenol than the toluene-containing stream; separating at least one para-xylene-enriched stream from the reactor effluent stream; and separating from the at least one para-xylene enriched stream at least one toluene-enriched stream and at least one para-xylene-product stream. An apparatus for carrying out such a process is also described.

32 Claims, 1 Drawing Sheet

(56) References Cited

U.S. PATENT DOCUMENTS

| 2011/0137099 A1* | 6/2011 | Ghosh .................... C07C 2/864 585/467 |
| 2012/0273392 A1* | 11/2012 | Serban .................. C10G 59/02 208/63 |
| 2012/0316375 A1 | 12/2012 | Zheng et al. |
| 2013/0324780 A1 | 12/2013 | Ou et al. |
| 2016/0115094 A1 | 4/2016 | Dakka et al. |
| 2016/0115103 A1 | 4/2016 | Dakka et al. |

OTHER PUBLICATIONS

Dodgson, Ivor et al., "A Low Cost Phenol to Cyclohexanone Process," Chemistry & Industry, 1989, pp. 830-833.

Wydra, M., et al. "Selective Hydrogenation of 4-Substituted Phenol Derivatives to the Cyclohexanone Analogs-Catalyst Optimization and Kinetics" Chemie Injenieur Technik, vol. 74, No. 6, pp. 800-804, 2002.

Non-Final Office Action for U.S. Appl. No. 14/872,468, dated Nov. 28, 2017, 8 pages.

* cited by examiner

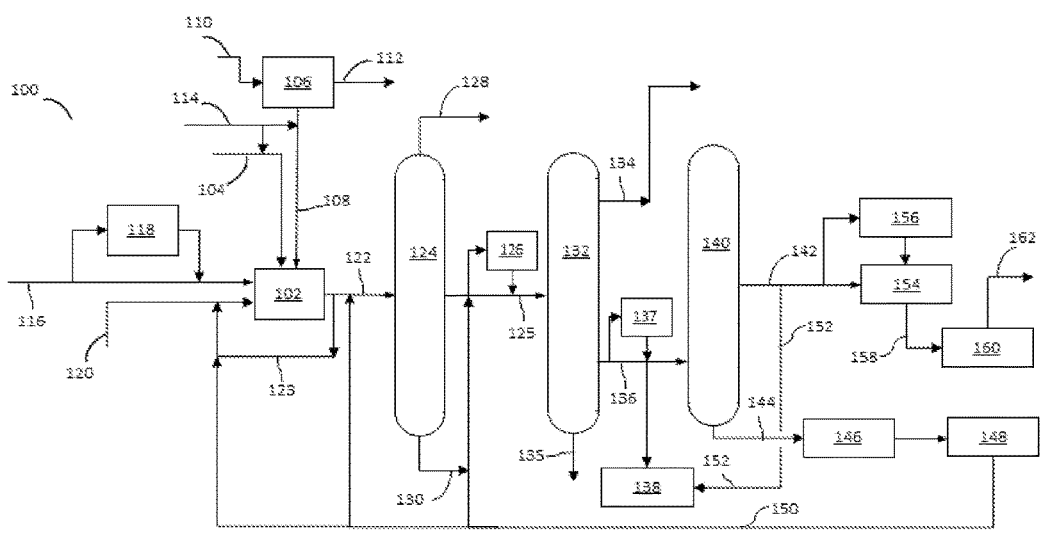

PROCESS AND APPARATUS FOR THE
CONVERSION OF HYDROCARBONS

CROSS-REFERENCE TO RELATED
APPLICATIONS

This application claims the benefit of U.S. Provisional Application No. 62/069,049 filed Oct. 27, 2014, herein incorporated by reference in its entirety.

FIELD

Embodiments of the disclosure relate to processes and apparatus for the conversion of hydrocarbons, particularly toluene-containing hydrocarbon streams, to xylenes, particularly para-xylene and products made therefrom.

BACKGROUND

Of the aromatic $C_8$ isomers, including the three xylene isomers and ethylbenzene, para-xylene is of particularly high value since para-xylene is useful in the manufacture of terephthalic acid, used in synthetic fibers and resins. Refinery and chemical plant streams containing the aromatic $C_8$ isomers typically contain, at thermodynamic equilibrium, only about 22-24 wt % para-xylene, based on the weight of the xylene isomers in the stream. Separation of para-xylene from the other $C_8$ isomers requires superfractionation and/or multistage refrigeration steps and/or adsorptive separation, all of which are energy intensive.

One known method for producing para-xylene selectively involves the alkylation of toluene and/or benzene with methanol and/or dimethyl ether (DME) over a solid acid catalyst. Selectivities to para-xylene in excess of 90 wt % (based on total $C_8$ aromatic product) have been reported by reacting toluene with methanol in the presence of a catalyst comprising a porous crystalline material, preferably a medium-pore zeolite and particularly ZSM-5, having a Diffusion Parameter for 2,2 dimethylbutane of about 0.1-15 sec$^{-1}$ when measured at a temperature of 120° C. and a 2,2 dimethylbutane pressure of 60 torr (8 kPa).

Known processes suffer from the presence of undesirable by-products, particularly phenol, which act as free-radical reaction inhibitors in the subsequent oxidative conversion of para-xylene to terephthalic acid and therefore substantially increase the reaction time of the para-xylene oxidation.

A method of reducing or eliminating such free-radical inhibitors in the para-xylene stream would be beneficial. A method wherein the free-radical inhibitors are converted to free-radical initiators to promote the subsequent oxidation reaction would also be beneficial.

SUMMARY

It has been found that deleterious effects on downstream processes of the presence of oxygenate free-radical reaction inhibitors in the para-xylene stream may be reduced by treatment of the catalyst with an inert atmosphere and a reducing atmosphere, thereby reducing the presence of undesirable catalyst impurities that are believed to produce oxygenate free-radical reaction inhibitors. Residual amounts of the oxygenates are converted to a ketone form, e.g., phenol to cyclohexanone. Surprisingly, the conversion may be performed in a single reactor with a combined alkylation and hydrogenation catalyst to provide both the aromatic alkylation and the selective oxygenate hydrogenation. While the alkylation and hydrogenation may be sequentially performed, a benefit of the present disclosure is that by careful selection and modification of the alkylation and hydrogenation catalysts, the hydrogenation of the oxygenate may be performed in the same reactor as the alkylation reaction without unacceptable loss in para-xylene production.

BRIEF DESCRIPTION OF THE DRAWINGS

FIG. 1 schematically illustrates a combined hydrocarbon conversion process according to an aspect of the disclosure.

DETAILED DESCRIPTION

All numerical values within the detailed description and the claims herein are modified by "about" or "approximately" the indicated value, and take into account experimental error and variations that would be expected by a person having ordinary skill in the art.

According to aspects of the disclosure, there is provided a method for the purification of an aromatic hydrocarbon process stream comprising para-xylene and phenol. The method includes contacting an aromatic hydrocarbon process stream with a hydrogenation catalyst under hydrogenation conditions to provide a hydrogenation effluent having a lower concentration of phenol than the aromatic hydrocarbon process stream. The aromatic hydrocarbon process stream comprises an effluent stream of a toluene alkylation process, e.g., comprising $C_8$ aromatics, particularly para-xylene, more particularly where the para-xylene is present in higher than equilibrium amounts. The toluene alkylation and phenol hydrogenation may be performed sequentially or contemporaneously. Thus, in particular aspects, the toluene alkylation is performed in the presence of a hydrogenation catalyst that hydrogenates the phenol by-product formed during the alkylation.

For the purposes of this disclosure and the claims thereto, the new numbering scheme for the Periodic Table Groups is used as described in Chemical and Engineering News, 63(5), p. 27 (1985). Therefore, a "Group 4 metal" is an element from Group 4 of the Periodic Table, e.g., Hf, Ti, or Zr.

As used herein, references to a "reactor" shall be understood to include both distinct reactors as well as reaction zones within a single reactor apparatus. In other words and as is common, a single reactor may have multiple reaction zones. Where the description refers to a first and second reactor, the person of ordinary skill in the art will readily recognize such reference includes a single reactor having first and second reaction zones. Likewise, a first reactor effluent and a second reactor effluent will be recognized to include the effluent from the first reaction zone and the second reaction zone of a single reactor, respectively.

As used herein, the phrase "at least a portion of" means >0 wt %, e.g., ≥5.0 wt %, 10.0 wt %, ≥20.0 wt %, ≥30.0 wt %, ≥40.0 wt %, ≥50.0 wt %, ≥60.0 wt %, ≥70.0 wt %, ≥80.0 wt %, ≥90.0 wt %, ≥95.0 wt %, or ≥99.0 wt %, of the process stream or composition to which the phrase refers. Additionally or alternatively, the phase "at least a portion of" means ≤100 wt %, e.g., ≤99.0 wt %, ≤95.0 wt %, ≤90.0 wt %, ≤80.0 wt %, ≤70.0 wt %, ≤60.0 wt %, ≤50.0 wt %, ≤40.0 wt %, ≤30.0 wt %, ≤20.0 wt %, ≤10.0 wt %, or ≤5.0 wt %. Ranges of the phrase "at least a portion of" that are expressly disclosed include any combination of the above enumerated values.

As used herein, the term "oxygenate," "oxygenate composition," and the like refer to oxygen-containing compounds having 1 to about 50 carbon atoms, preferably 1 to about 20 carbon atoms, more preferably 1 to about 10 carbon atoms, and most preferably 1 to about 4 carbon atoms.

Exemplary oxygenates include alcohols, ethers, carbonyl compounds, e.g., aldehydes, ketones and carboxylic acids, and mixtures thereof. Particular oxygenates methanol, ethanol, dimethyl ether, diethyl ether, methylethyl ether, di-isopropyl ether, dimethyl carbonate, dimethyl ketone, formaldehyde, and acetic acid.

In any aspect, the oxygenate may comprise one or more alcohols, preferably alcohols having 1 to about 20 carbon atoms, more preferably 1 to about 10 carbon atoms, or most preferably 1 to about 4 carbon atoms. The alcohols useful as first mixtures may be linear or branched, substituted or unsubstituted aliphatic alcohols and their unsaturated counterparts. Non-limiting examples of such alcohols include methanol, ethanol, propanols (e.g., n-propanol, isopropanol), butanols (e.g., n-butanol, sec-butanol, tert-butyl alcohol), pentanols, hexanols, etc., and mixtures thereof. In any aspect described herein, the oxygenate may comprise one or more of methanol, and/or ethanol, particularly methanol. In any aspect, the oxygenate may be methanol and/or dimethyl ether.

The oxygenate, particularly where the oxygenate comprises an alcohol (e.g., methanol), may optionally be subjected to dehydration, e.g., catalytic dehydration over e.g., γ-alumina. Further optionally, at least a portion of any methanol and/or water remaining in the first mixture after catalytic dehydration may be separated from the first mixture. If desired, such catalytic dehydration may be used to reduce the water content of reactor effluent before it enters a subsequent reactor or reaction zone.

In any aspect, one or more other compounds may be present in the oxygenate. Typically, although not necessarily, such compounds include one or more heteroatoms other than oxygen. Some such compounds include amines, halides, mercaptans, sulfides, and the like. Particular such compounds include alkyl-mercaptans (e.g., methyl mercaptan and ethyl mercaptan), alkyl-sulfides (e.g., methyl sulfide), alkyl-amines (e.g., methyl amine), and alkyl-halides (e.g., methyl chloride and ethyl chloride). In any aspect, the first mixture includes one or more of ≥1.0 wt % acetylene, pyrolysis oil or aromatics, particularly $C_6$ and/or $C_7$ aromatics.

The Hydrocarbon Conversion Process

The process for forming the reactor effluent stream can employ any aromatic feedstock comprising ≥5.0 wt % toluene and/or benzene, although in general it is preferred that the aromatic feed contains at least 90 wt %, especially at least 99 wt %, of benzene, toluene or a mixture thereof. An aromatic feed containing at least 99 wt % toluene is particularly desirable. Similarly, although the composition of the oxygenate-containing feed, e.g., methanol, is not critical, it is generally desirable to employ feeds containing at least 90 wt %, especially at least 99 wt %, of oxygenate.

Catalyst/Reactor Treatment

In embodiments of the disclosure, the method begins by contacting in a reactor an inert gas with one or more catalyst compositions suitable for methylation of toluene and hydrogenation of phenol. Contacting the inert gas, e.g., nitrogen, argon, and mixtures thereof, with the one or more catalyst compositions may include flowing the inert gas through the reactor. The amount of inert gas used should be sufficient to reduce the presence of oxygen in the reactor to desirably lower levels. Conditions for contacting the inert gas with the one or more catalyst compositions are described in Japanese Laid Open Patent Application JP58164527A, incorporated herein by reference in its entirety.

Embodiments of the disclosure also include, either before or after the inert gas step, contacting a reducing agent with the one or more catalyst compositions under conditions suitable for reducing metal oxide content of the catalyst composition. Exemplary conditions for inert gas treatment Exemplary conditions for contacting with the reducing agent include contacting the one or more catalyst compositions with the reducing agent at a reactor temperature of 200 to 600° C., preferably 250 to 550° C. Particularly useful reducing agents comprise molecular hydrogen gas. Usually, this reduction treatment is performed after the catalyst has been filled into a reactor.

Additionally or alternatively, the method may include regenerating the one or more catalyst compositions by treatment with oxygen as described in Int'l Pat. Application Pub. No. WO2012074613, the disclosure of which is incorporated herein by reference in its entirety, prior to contacting with the inert gas and/or contacting with the reducing agent.

Alkylation Process and Catalyst Composition

The alkylation process for forming the aromatic hydrocarbon stream can employ any aromatic feedstock comprising ≥5.0 wt % toluene and/or benzene, although in general it is preferred that the aromatic feed contains at least 90 wt %, especially at least 99 wt %, of benzene, toluene or a mixture thereof. An aromatic feed containing at least 99 wt % toluene is particularly desirable. Similarly, although the composition of the methanol-containing feed, i.e., first mixture, is not critical, it is generally desirable to employ feeds containing at least 90 wt %, especially at least 99 wt %, of methanol.

The catalyst employed in the alkylation process is generally a porous crystalline material and, in one preferred aspect, is a porous crystalline material having a Diffusion Parameter for 2,2 dimethylbutane of about 0.1-15 sec$^{-1}$ when measured at a temperature of 120° C. and a 2,2 dimethylbutane pressure of 60 torr (8 kPa).

As used herein, the Diffusion Parameter of a particular porous crystalline material is defined as $D/r^2 \times 10^6$, wherein D is the diffusion coefficient (cm$^2$/sec) and r is the crystal radius (cm). The diffusion parameter can be derived from sorption measurements provided the assumption is made that the plane sheet model describes the diffusion process. Thus for a given sorbate loading Q, the value $Q/Q_{eq}$, where $Q_{eq}$ is the equilibrium sorbate loading, is mathematically related to $(Dt/r^2)^{0.5}$ where t is the time (sec) required to reach the sorbate loading Q. Graphical solutions for the plane sheet model are given by J. Crank in "The Mathematics of Diffusion", Oxford University Press, Ely House, London, 1967.

The porous crystalline material is preferably a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene and p-xylene. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst.

Particular examples of suitable medium pore zeolites include ZSM-5, ZSM-11, ZSM-12, ZSM-22, ZSM-23, ZSM-35, and ZSM-48, with ZSM-5 and ZSM-11 being particularly preferred. In one aspect, the zeolite employed in the process of the disclosure is ZSM-5 having a silica to alumina molar ratio of at least 250, as measured prior to any treatment of the zeolite to adjust its diffusivity.

Zeolite ZSM-5 and the conventional preparation thereof are described in U.S. Pat. No. 3,702,886. Zeolite ZSM-11 and the conventional preparation thereof are described in U.S. Pat. No. 3,709,979. Zeolite ZSM-12 and the conventional preparation thereof are described in U.S. Pat. No. 3,832,449. Zeolite ZSM-23 and the conventional preparation thereof are described U.S. Pat. No. 4,076,842. Zeolite ZSM-35 and the conventional preparation thereof are described in U.S. Pat. No. 4,016,245. ZSM-48 and the conventional preparation thereof are taught by U.S. Pat. No. 4,375,573. The entire disclosures of these U.S. patents are incorporated herein by reference.

In addition to the medium-pore size aluminosilicate zeolites, other medium pore acidic metallosilicates, such as silicoaluminophosphates (SAPOs), can be used in the present process. Non-limiting examples of zeolites useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, and SAPO-56.

The medium pore zeolites described above are preferred for the present process since the size and shape of their pores favor the production of p-xylene over the other xylene isomers. However, conventional forms of these zeolites have Diffusion Parameter values in excess of the 0.1-15 $\sec^{-1}$ range desired for the present process. Nevertheless, the required diffusivity can be achieved by severely steaming the zeolite so as to effect a controlled reduction in the micropore volume of the catalyst to not less than 50%, and preferably 50-90%, of that of the unsteamed catalyst. Reduction in micropore volume is monitored by measuring the n-hexane adsorption capacity of the zeolite, before and after steaming, at 90° C. and 75 torr n-hexane pressure.

Steaming to achieve the desired reduction in the micropore volume of the porous crystalline material can be effected by heating the material in the presence of steam at a temperature of at least about 950° C., preferably about 950 to about 1075° C., and most preferably about 1000 to about 1050° C. for about 10 minutes to about 10 hours, preferably from 30 minutes to 5 hours.

To effect the desired controlled reduction in diffusivity and micropore volume, it may be desirable to combine the porous crystalline material, prior to steaming, with at least one oxide modifier, preferably selected from oxides of the elements of Groups 2, 3, 4, 5, 13, 14, 15, and 16 of the Periodic Table. Conveniently, the at least one oxide modifier is selected from oxides of boron, magnesium, calcium, lanthanum and preferably phosphorus. In some cases, it may be desirable to combine the porous crystalline material with more than one oxide modifier, for example a combination of phosphorus with calcium and/or magnesium, since in this way it may be possible to reduce the steaming severity needed to achieve a target diffusivity value. The total amount of oxide modifier present in the catalyst, as measured on an elemental basis, may be between about 0.05 and about 20 wt %, such as between about 0.1 and about 10 wt %, based on the weight of the final catalyst.

Where the modifier includes phosphorus, incorporation of modifier in the alkylation catalyst is conveniently achieved by the methods described in U.S. Pat. Nos. 4,356,338, 5,110,776, 5,231,064 and 5,348,643, the entire disclosures of which are incorporated herein by reference. Treatment with phosphorus-containing compounds can readily be accomplished by contacting the porous crystalline material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt %. Such phosphorous-stabilized catalyst compositions are well-known to provide hydrothermal stability. The phosphorous can be incorporated after formulation of the zeolite (such as by extrusion) to form self-bound catalyst particles. Optionally, a self-bound catalyst can be steamed after extrusion. Such compositions are particularly useful where the reactor feed includes a significant amount of water, e.g., ≥5 wt % $H_2O$.

Representative phosphorus-containing compounds which may be used to incorporate a phosphorus oxide modifier into the catalyst of the disclosure include derivatives of groups represented by $PX_3$, $RPX_2$, $R_2PX$, $R_3P$, $X_3PO$, $(XO)_3PO$, $(XO)_3P$, $R_3P=O$, $R3P=S$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as phenyl radical, and X is hydrogen, R, or halide. These compounds include primary, $RPH_2$, secondary, $R_2PH$, and tertiary, $R_3P$, phosphines such as butyl phosphine, the tertiary phosphine oxides, $R_3PO$, such as tributyl phosphine oxide, the tertiary phosphine sulfides, $R_3PS$, the primary, $RP(O)(OX)_2$, and secondary, $R_2P(O)OX$, phosphonic acids such as benzene phosphonic acid, the corresponding sulfur derivatives such as $RP(S)(SX)_2$ and $R_2P(S)SX$, the esters of the phosphonic acids such as dialkyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2PDX$, such as diethylphosphinous acid, primary, $(RO)P(OX)_2$, secondary, $(RO)_2PDX$, and tertiary, $(RO)_3P$, phosphites, and esters thereof such as the monopropyl ester, alkyl dialkylphosphinites, $(RO)PR_2$, and dialkyl alkyphosphinite, $(RO)_2PR$, esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)2PSX$, $(RS)_3P$, $(RS)PR_2$, and $(RS)_2PR$. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, $(RO)PCl_2$, dialkylphosphoro-chloridites, $(RO)_2PCl$, dialkylphosphinochloroidites, $R_2PCl$, alkyl alkylphosphonochloridates, $(RO)(R)P(O)Cl$, dialkyl phosphinochloridates, $R_2P(O)Cl$, and $RP(O)Cl_2$. Applicable corresponding sulfur derivatives include $(RS)PCl_2$, $(RS)_2PCl$, $(RS)(R)P(S)Cl$, and $R_2P(S)Cl$.

Particular phosphorus-containing compounds include ammonium phosphate, ammonium dihydrogen phosphate, diammonium hydrogen phosphate, diphenyl phosphine chloride, trimethylphosphite, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate, and other alcohol-$P_2O_5$ reaction products.

Representative boron-containing compounds which may be used to incorporate a boron oxide modifier into the catalyst of the disclosure include boric acid, trimethylborate, boron oxide, boron sulfide, boron hydride, butylboron dimethoxide, butylboric acid, dimethylboric anhydride, hexamethylborazine, phenyl boric acid, triethylborane, diborane and triphenyl boron.

Representative magnesium-containing compounds include magnesium acetate, magnesium nitrate, magnesium benzoate, magnesium propionate, magnesium 2-ethylhexoate, magnesium carbonate, magnesium formate, magnesium oxylate, magnesium bromide, magnesium hydride, magnesium lactate, magnesium laurate, magnesium oleate, magnesium palmitate, magnesium salicylate, magnesium stearate and magnesium sulfide.

Representative calcium-containing compounds include calcium acetate, calcium acetylacetonate, calcium carbonate, calcium chloride, calcium methoxide, calcium naphthenate, calcium nitrate, calcium phosphate, calcium stearate and calcium sulfate.

Representative lanthanum-containing compounds include lanthanum acetate, lanthanum acetylacetonate, lanthanum carbonate, lanthanum chloride, lanthanum hydroxide, lanthanum nitrate, lanthanum phosphate and lanthanum sulfate.

The porous crystalline material employed in the process of the disclosure may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. The materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt % of the composite.

The alkylation process can be conducted in any known reaction vessel but generally the methanol and aromatic feeds are contacted with the catalyst described above with the catalyst particles being disposed in one or more fluidized beds. Each of the methanol and aromatic feeds can be injected into the fluidized catalyst in a single stage. However, in one aspect, the methanol feed is injected in stages into the fluidized catalyst at one or more locations downstream from the location of the injection of the aromatic reactant into the fluidized catalyst. For example, the aromatic feed can be injected into a lower portion of a single vertical fluidized bed of catalyst, with the methanol being injected into the bed at a plurality of vertically spaced intermediate portions of the bed and the product being removed from the top of the bed. Alternatively, the catalyst can be disposed in a plurality of vertically spaced catalyst beds, with the aromatic feed being injected into a lower portion of the first fluidized bed and part of the methanol being injected into an intermediate portion of the first bed and part of the methanol being injected into or between adjacent downstream catalyst beds.

The conditions employed in the alkylation stage of the present process are not particularly constrained. Generally in the case of the methylation of toluene, the temperature is between about 500 and about 750° C., preferably between about 500 and about 700° C., and more preferably between about 500 and about 600° C. The alkylation may be conducted at any useful pressure. Typically the pressure is between about 1 atmosphere and about 1000 psig (between about 100 and about 7000 kPa), preferably between about 10 psig and about 200 psig (between about 170 and about 1480 kPa). The molar ratio of aromatic molecules (e.g., toluene) to moles of methanol (moles toluene/moles methanol) is typically at least about 0.2, preferably from about 0.2 to about 20. The weight hourly space velocity ("WHSV") for total hydrocarbon feed to the reactor(s) in the alkylation process is typically about 0.2 to about 1000, preferably about 0.5 to about 500 for the aromatic reactant, and preferably about 0.01 to about 100 for the combined methanol reagent stage flows, based on total catalyst in the reactor(s).

The effluent from the alkylation process typically comprises a mixture of aromatic molecules, particularly $C_{8+}$ aromatics and phenol. Typically the alkylation effluent comprises ≥about 25.0 wt % of aromatics, based on the weight the alkylation effluent. In any aspect, the alkylation effluent may comprise ≥about 25.0 wt % para-xylene based on the weight of the aromatics. For example, the amount of para-xylene in the aromatics of the hydrocarbon component of the product stream may be about 25.0 to 100.0 wt %, preferably about 30.0 to 100.0 wt %, and more preferably about 40.0 to 100.0 wt %. Ranges expressly disclosed include combinations of any of the above-enumerated values.

The alkylation effluent also comprises a minor amount of phenol. While the amount of phenol is not particularly limited, the presence of phenol acts as a free radical inhibit in subsequent reaction. Thus, lower amounts of phenol are preferred. In particular aspects, the amount of phenol is ≤about 25.0 ppmw, preferably ≤about 10.0 ppmw, more preferably ≤about 5.0 ppmw, most preferably ≤about 1.0 ppmw, and ideally ≤about 0.5 ppmw. Ranges of the amount of phenol in the alkylation effluent expressly disclosed include ranges bound by the upper and lower values of phenol content enumerated above, e.g., about 0.5 to about 25 ppm, about 0.5 to about 10.0 ppm, about 1.0 to about 5.0 ppm, etc.

Hydrogenation Process and Catalyst Composition

In an aspect of the disclosure, the alkylation effluent is hydrogenated to convert at least a portion of the phenol contained therein to cyclohexanone. The hydrogenation may be carried out by any suitable process. Cyclohexanone can be conventionally prepared from phenol by catalytic hydrogenation in a phenol hydrogenation reactor using any known hydrogenation catalyst. The reaction can be carried out in the liquid phase or the vapor phase as described in Kirk-Othmer Encyclopedia of Chemical Technology, e.g., $3^{rd}$ Edition, Vol. 7 (1979) pp. 410-416; I. Dodgson et al. "A low Cost Phenol to Cyclohexanone Process", Chemistry & Industry 18 Dec. 1989, pp. 830-833; A. C. Dimian and C. S. Bildea "Chemical Process Design, Computer-Aided Case Studies", Wiley-VCH Verlag GmbH&Co. KGaA, Weinheim, Germany, Chapter 5, pp. 129-172; or M. T. Musser "Cyclohexanol and Cyclohexanone", Ullmann's Encyclopedia of Industrial Chemistry ($7^{th}$ Edition, 2007), each of which is incorporated herein by reference. The use of a fixed-bed, moving-bed, or fluid bed reactor is envisioned.

The reaction method when carrying out the present disclosure may be any of a batch method, a semi-batch method or a continuous flow method. With the catalyst being in a solid state, the form of reaction may be any of liquid phase, vapor phase, liquid-vapor mixed phase, solid phase, or supercritical fluid phase, or any combination of these may be used. For example, with the catalyst being in a solid state, the reaction may be carried out in any form out of liquid-vapor mixed phase, solid-liquid-vapor mixed phase, liquid-supercritical fluid mixed phase or supercritical fluid phase. Furthermore, the reaction may be carried out under normal pressure or under a pressurized state. From the viewpoint of the reaction efficiency, using supercritical carbon dioxide is recommended, but the present disclosure is not limited thereto.

For example, in an aspect of the disclosure the effluent of the alkylation process may be contacted in the presence of a hydrogen source, e.g., $H_2$, with a hydrogenation catalyst comprising one or more catalytically active metals. A catalyst comprising at least one metallic element selected from the platinum group metals Pd, Os, Ir and Pt, or metallic elements such as Ni, Co, Fe, Zn, Cu, Mn, Pb, Cd, Cr, Ag, Au, Hg, Ga, In, Ge, Sn, Ti, Al and Si may be used. In particular aspects, the above-enumerated elements may be combined with a Group 2 elements Ca, Mg, Sr and Ba, and/or one or more alkali metals, e.g., Li, Na, K, Rb and Cs, particularly in combination with palladium, platinum, rhodium and/or ruthenium or alloying therewith can also be effectively used in the present disclosure. A catalyst comprising palladium is particularly useful in aspects of the disclosure.

In particular aspects, it may be desirable to reduce the activity of the catalyst to hydrogenate the para-xylene. Thus, additionally or alternatively, in any aspect the hydrogenation catalyst may include a para-xylene hydrogenation suppressing agent to suppress the hydrogenation of para-xylene. The suppressing agent is typically a metal different from the metal of the catalyst and may comprise one or more Group 8-Group 15 elements. Exemplary Group 8-Group 15 elements include Fe, Ru, Os, Co, Ru, Ir, Ni, Pd, Pt, Cu, Ag, Au, Zn, Cd, B, Al, Ga, In, C, Si, Ge, Sn, Pb, N, P, As, Sb, and Bi, particularly Fe, Sn, and/or Bi. Such catalysts are described in Int'l. App. No. WO 2012134552, incorporated herein by reference in its entirety.

In the present disclosure, for example, activated charcoal, alumina, magnesia, silica, silica alumina, zirconia, titania, zeolite, clay, kaolin, talc, bentonite, or a gel or sol thereof can be, but need not be, suitably used as a carrier in the supported rhodium and/or ruthenium catalyst. A mixture of suitable ones of these carriers may also be used in the catalyst. There are no particular limitations on the carrier, so long as the carrier does not unacceptably hamper the reaction or the catalytic activity; even a carrier that exhibits some degree of catalytic activity toward the reaction can be used. Typically, the metal (other than metal associated with the support) is present in supported catalyst compositions at a concentration of 0.5-5 wt %, based on the total weight of the catalyst.

Typically, the hydrogenation catalyst is preferably activated before use by heat treatment in a stream of a gas such as hydrogen, nitrogen, argon, carbon dioxide, oxygen or air. The treatment temperature during the heating treatment is generally in a range of 50 to 700° C., preferably 80 to 600° C., more preferably 80 to 500° C., most preferably 100 to 500° C. A treatment temperature less than 50° C. is undesirable, since adsorbed matter will not be desorbed sufficiently. Moreover, a treatment temperature exceeding 700° C. is undesirable, since the structure of the carrier in the catalyst will become liable to break up, and hence the surface area will tend to drop, and moreover agglomeration of the metal particles will occur. The activation treatment time is influenced by the amount of matter adsorbed on the surface and the treatment temperature, and hence there are no particular limitations on this treatment time, although a treatment time of 0.1 to 100 hours is generally suitable.

In an aspect, the hydrogenation may be conducted as described by Liu et al., "Selective Phenol Hydrogenation to Cyclohexanone Over a Dual Supported Pd-Lewis Acid Catalyst, Science, Vol. 326, No. 5957, pp. 1250-1252 (November 2009). Alternatively, the effluent of the alkylation process may be passed over a hydrogenation catalyst as described by Wang et al., in "Highly Selective Hydrogenation of Phenol and Derivatives over a Pd-Carbon Nitride Catalyst in Aqueous Media," *J. Am. Chem. Soc.*, 2011, Vol. 133, No. 88, pp. 2362-2365.

In another aspect, the hydrogenation may be carried out as described in U.S. Pat. No. 7,453,018, incorporated by reference herein in its entirety. In such a hydrogenation, the molecular sieve is modified by the addition of a hydrogenation component, wherein at least one of the following conditions is met: (a) the selectivated molecular sieve has an alpha value of less than 100 prior to the addition of the hydrogenation component, or (b) the selectivated and hydrogenated catalyst has an alpha value of less than 100.

The amount of the hydrogenation catalyst used is not critical. In the case of a batch reaction for example, the amount of the catalyst used relative to the phenol present in the effluent from the alkylation reaction may be in a range of 0.01 to 200 wt %, preferably 0.05 to 100 wt %, more preferably 0.05 to 50 wt %, yet more preferably 0.1 to 30 wt %, most preferably 0.1 to 10 wt %. The amount of the catalyst is set as appropriate in accordance with the reaction method, the reaction conditions, the types of the raw material and the catalyst, and so on, but if the amount of the catalyst used is too low, then there will be a substantial drop in the progress of the reaction, and if the amount of the catalyst used is too high, then problems may arise such as the efficiency of contact and so on dropping, and the manufacturing cost increasing.

Additionally or alternatively, water may be fed into the reactor continuously or intermittently. The weight to weight ratio of water fed into the reactor to phenol fed into the reactor on average being 0.1 or less. Alumina support may be particularly suitable in aspects wherein water and the compound to be hydrogenated are fed into the reactor as a vapor. Activated carbon is in particular preferred where water and the compound to be hydrogenated are fed into the reactor as a liquid.

In any aspect, at least a portion of the effluent of the alkylation process may be provided to the reactor along with a co-feed. The co-feed is selected to increase selectivity of the catalyst toward phenol hydrogenation. Exemplary co-feeds include CO and $H_2S$.

The hydrogenation reaction is typically carried out at temperatures from about 25 to about 250° C. The temperature may be selected to balance the reaction rate, selectivity, and yield. The hydrogenation reaction is generally performed at a total pressure of about 0.1 to 150 MPa, preferably about 10 to about 150 MPa, and most preferably about 25 to 100 MPa. The reaction time is not particularly limited. Exemplary reaction times may be about 1 minute to 10 hours, preferably about 5 minutes to 5 hours, and more preferably about 5 minutes to about 2 hours. When carrying out the hydrogenation, there are no particular limitations on the composition charged in of the hydrogen and the phenol. High conversion ratios are generally improved by a relatively high molar ratio of hydrogen to phenol. Thus, in any aspect, the molar ratio of the hydrogen to the phenol is generally 1.0 to 1000.

The hydrogenation effluent typically comprises aromatics as described above. The phenol content of the hydrogenation effluent, however, is less than that of the alkylation effluent, based on the total weights of the alkylation and hydrogenation effluents. In any aspect, the hydrogenation effluent comprises ≤about 25.0 ppmw, preferably ≤about 10.0 ppmw, more preferably ≤about 5.0 ppmw, most preferably ≤about 1.0 ppmw, and ideally ≤about 0.5 ppmw. The hydrogenation effluent may also be characterized by the ratio of the amount of phenol therein to the amount of phenol in the alkylation effluent. In any aspect, the ratio of the wt % phenol in the hydrogenation effluent to the wt % of phenol in the alkylation effluent may be about 0.001 to about 0.95 wt %. Ranges of the ratio of the wt % phenol in the hydrogenation effluent to the wt % of phenol in the alkylation effluent expressly disclosed include ranges bound by the upper and lower values.

One skilled in the art will realize that because the phenol in the alkylation effluent is converted primarily to cyclohexanone, the hydrogenation effluent may comprise ≤about 25.0 ppmw cyclohexanone, preferably ≤about 10.0 ppmw, more preferably ≤about 5.0 ppmw, most preferably ≤about 1.0 ppmw, and ideally ≤about 0.5 ppmw.

Combined Alkylation/Hydrogenation

In another aspect of the disclosure, the aromatic feedstock is provided to a reaction vessel that includes, in addition to an alkylation catalyst above, a hydrogenation catalyst described above. In such aspects, generally, the reaction parameters, i.e., temperature, pressure, WHSV, etc., of the alkylation reaction are used. A hydrogen source is co-fed along with the oxygenate, i.e., methanol, and the aromatic feedstock, i.e., toluene, benzene or mixtures thereof.

The hydrogenation metal catalyst may be added to the alkylation catalyst to form a combined multifunctional catalyst that simultaneously hydrogenates phenol as the phenol is produced in the alkylation reaction. The combined alkylation/hydrogenation catalyst has the added benefit of improving the catalyst stability by hydrogenating reaction intermediates that are coke precursors. To prevent the hydrogenation of para-xylene, a para-xylene hydrogenation suppressing agent as described above may be included in the catalyst. Additionally, in any aspect of the combined alkylation/hydrogenation, a phenol hydrogenation selectivity co-feed, e.g. CO and $H_2S$, may be provided as described above. In the absence of providing a phenol hydrogenation selectivity co-feed, there may still be a phenol hydrogenation selectivity effect from CO formed from methanol decomposition in the reactor.

The effluent from the combined alkylation/hydrogenation process may comprise a mixture of aromatic molecules, particularly $C_{8+}$ aromatics and phenol. Typically the alkylation/hydrogenation effluent comprises ≥about 25.0 wt % of aromatics, based on the weight the alkylation/hydrogenation effluent. In any aspect, the alkylation/hydrogenation effluent may comprise ≥about 25.0 wt % para-xylene based on the weight of the aromatics. For example, the amount of para-xylene in the aromatics of the hydrocarbon component of the product stream may be about 25.0 to 100.0 wt %, preferably about 30.0 to 100.0 wt %, and more preferably about 40.0 to 100.0 wt %. Ranges expressly disclosed include combinations of any of the above-enumerated values.

The effluent from the combined alkylation/hydrogenation process may also have a phenol content of ≤about 25.0 ppmw, preferably ≤about 10.0 ppmw, more preferably ≤about 5.0 ppmw, most preferably ≤about 1.0 ppmw, and ideally ≤about 0.5 ppmw. Ranges of the amount of phenol in the alkylation effluent expressly disclosed include ranges bound by the upper and lower values of phenol content enumerated above, e.g., about 0.5 to about 25 ppm, about 0.5 to about 10.0 ppm, about 1.0 to about 5.0 ppm, etc.

Likewise, the effluent from the combined alkylation/hydrogenation may have a cyclohexanone content of comprise ≤about 25.0 ppmw cyclohexanone, preferably ≤about 10.0 ppmw, more preferably ≤about 5.0 ppmw, most preferably ≤about 1.0 ppmw, and ideally ≤about 0.5 ppmw.

FIG. 1 schematically illustrates an exemplary process 100. In process 100, a reactor 102 having a catalyst composition therein is purged with a inert gas, e.g., nitrogen, argon, or mixtures thereof, from conduit 104 to reduce residual oxygen content in the reactor and catalyst composition. A catalyst regeneration unit 106 is typically present to provide a convenient source of fresh catalyst. Typically an oxygen-containing gas, e.g., air, is provided to the regeneration unit 106 via conduit 110 and flue gas exits via conduit 112. To reduce the concentration of undesirable oxidized species in the catalyst prior to initiating the reaction and/or when new new/regenerated catalyst is added to reactor 102, a reducing agent, e.g., molecular hydrogen, is supplied, e.g. via conduit 114 to reactor 102 directly via conduit 104 and/or to the catalyst composition as it passes from the catalyst regeneration unit 106 to the reactor, e.g., via conduit 108. Optionally reactor 102 is subjected to a descaling procedure wherein the reactor pressure is repeatedly increased and decreased at a rate to trace metal build up in the unit. Optionally impurities (e.g., Fe, V, Co, Mn-containing compounds, etc) in the catalyst composition may be reduced by maintaining the catalyst composition within specification by providing fresh catalyst portions and/or removal of contaminated catalysts from system as appropriate.

Feed comprising an oxygenate, e.g., methanol, is provided via line 116 to optional dehydration unit 118 or to reactor 102. An aromatic hydrocarbon feed comprising ≥5.0 wt % toluene and/or benzene is provided via line 120. Hydrogen may be supplied during the reaction either to reactor 102 directly to the reactor via line 114 or it may be combined with one or more of lines 104, 108, 116 and/or 120. Optionally, the phenol hydrogenation promoting co-feed may be provided to the reactor via line 120 or it may be combined with one or more of lines 104, 108, 116 and/or 120.

Reactor 102 is operated under conditions suitable for alkylating the toluene and hydrogenating the phenol byproduct as described above. Thus, reactor 102 has therein a catalyst composition suitable for alkylating the toluene, in the toluene-containing feed with the methanol from line 116. Reactor 102 may be any type of reactor, however, in particular embodiments, reactor 102 is a fluidized bed reactor.

A reactor effluent stream 122 from the reactor 102 may be provided to a first separation unit 124. The reactor effluent stream 122 comprises para-xylene and has a lower concentration of phenol than stream 120. The relative concentration of phenol should be determined by comparing the concentration of phenol between at the reactor inlet to the concentration of the reactor outlet. First separation unit 114 may be any separation means or process suitable to separate at least one para-xylene-enriched stream 125 from the reactor effluent stream 122. Some suitable such separation units comprise, e.g., a distillation tower, a simulated moving-bed separation unit, a high pressure separator, a low pressure separator, a flash drum, combinations thereof, etc. In particular aspects, the first separation unit is a separation unit other than a distillation tower. In particular aspects, the first separation unit is a three-phase separator. The para-xylene enriched stream 125 comprises $C_{8+}$ aromatics, particularly para-xylene, meta-xylene, ortho-xylene, ethylbenzene. Optionally, the first separation unit may separate from the reactor effluent stream a light gas fraction 128 and/or a water-containing fraction 130. In particular embodiments, the pH of the reactor effluent stream is raised, e.g., by adding caustic, sufficient to convert phenol to sodium phenolates, which then dissolve and leave system via fraction 130. One such method is described in U.S. Patent Publication No. 2012/0316375.

Optionally, at least a portion of effluent stream 122 may be recycled, e.g., via conduit 123, and combined with the aromatic hydrocarbon in conduit 120.

The para-xylene enriched stream 125 is directed to second separation unit 132, optionally via first phenol adsorbing unit 126. Phenol adsorbing unit 126 includes a phenol adsorbent composition. Adsorbents selective for phenol are known in the art and any such composition may be used. Some suitable materials used to remove phenol from the process stream are described in U.S. Patent Publication No. 2013/0324780 and include alumina, silica, molecular sieves, zeolites, basic organic resins, and mixtures thereof.

Second separation unit 132 may be any separation means or process suitable to separate at least one toluene-enriched stream 134 and at least one para-xylene-product stream 136 from the at least one para-xylene enriched stream 126. Some suitable such second separation units comprise, e.g., a distillation tower, a simulated moving-bed separation unit, a high pressure separator, a low pressure separator, a flash drum, combinations thereof, etc. In particular aspects, the second separation unit is a separation unit other than a distillation tower. In some embodiments, the second separation unit is configured to separate, e.g., using vapor-liquid equilibrium thermodynamic techniques, a phenol-containing heavy stream 135 from the least one para-xylene enriched stream 126.

At least a portion of para-xylene product stream 136 may be directed to a second phenol adsorbing unit 137. Like the first phenol adsorbing unit 126, phenol adsorbing unit 137 includes a phenol adsorbent composition.

The effluent therefrom phenol adsorbing unit 137 may be sent to a crude para-xylene storage 138 to crude recover para-xylene as is known in the art. Exemplary methods of subsequent purification may be described in one or more of U.S. Pat. Nos. 8,716,541; 8,697,929; 8,692,044; 8,569,559; 8,541,639; 8,529,757; 8,507,744; 8,502,008, each of which is incorporated herein by reference in its entirety.

Typically, however, the effluent from the second phenol adsorbing unit 137 or the para-xylene product stream 136 is provided to a third separator 140 that separates a primarily para-xylene containing stream 142 and para-xylene depleted stream 144. The third separator 140 may be any separator suitable for separating para-xylene and from aromatics-containing streams. In some embodiments, the third separator 140 may be referred to as a para-xylenepara-xylene recovery unit and may be configured to provide a para-xylene depleted stream 144 having phenol therein, e.g., via crystallization techniques as described in U.S. Pat. No. 8,252,967, which may be directed to isomerization unit 148 having a xylene isomerization catalyst therein and optionally via third phenol adsorbing unit 146 to contact the stream with a phenol adsorbent composition in the third phenol adsorbing unit 146 which may be the same or different from the phenol adsorbent composition used in the first or second phenol adsorbing units. Isomerization unit 148 may be a liquid phase isomerization unit or a gas phase isomerization unit. In particular embodiments, the isomerization unit 148 comprises a liquid phase isomerization unit and a gas phase isomerization unit. The isomerization unit 148 provides an isomerized stream 150, at least a portion of which may be recycled to the first separator 144, e.g., by combination with reactor effluent stream 122 and/or the second separator, e.g., by combination with least one para-xylene enriched stream 126.

At least a portion of the primarily para-xylene containing stream 142 may be directed to para-xylenepara-xylene recovery unit 138 via conduit 152. Additionally or alternatively, at least a portion of the primarily para-xylene containing stream 142 may be directed to oxidation unit 154 where it is contacted with a free radical under conditions effective to oxidize para-xylene therein to produce an oxidized effluent 156 comprising terephthalic acid. Optionally, the at least a portion of the stream 142 may be provided to a fourth phenol adsorbing unit 158 having an adsorbent selective for phenol. The adsorbent selective for phenol in the fourth phenol adsorbing unit 158 may be the same or different from the adsorbent selective for phenol used in the first, second and/or third phenol adsorbing units. The oxidized effluent 156 may be provided to recovery unit for recovering terephthalic acid therefrom, which may be removed from the process via conduit 162.

PCT/EP Clauses

1. A hydrocarbon conversion, comprising:
    a) contacting in at least a first reactor an inert gas with one or more catalyst compositions suitable for methylation of toluene and/or hydrogenation of phenol;
    b) contacting a reducing agent with the one or more catalyst compositions under conditions suitable for reducing metal oxide content of the first catalyst composition;
    c) contacting at least part of an aromatic hydrocarbon stream comprising ≥5.0 wt % toluene and/or benzene with a oxygenate in the presence of the first catalyst composition and under conditions effective to convert toluene to xylenes and produce a reactor effluent stream comprising para-xylene and having a lower concentration of phenol than the aromatic hydrocarbon stream;

d) separating in a first separator at least one para-xylene-enriched stream from the reactor effluent stream; and e) separating in a second separator from the at least one para-xylene enriched stream at least one toluene-enriched stream and at least one para-xylene-product stream.

2. The method of Clause 1, further comprising separating in a third separator a primarily para-xylene containing stream and para-xylene depleted stream from the at least one para-xylene-product stream.

3. The method of Clause 2, further comprising f) contacting at least a portion of primarily para-xylene containing stream with a free radical under conditions effective to oxidize at least a portion of the para-xylene to produce an oxidized effluent having terephthalic acid therein;

g) recovering terephthalic acid from the oxidized effluent.

4. The method of Clause 3, further comprising contacting the primarily para-xylene containing stream with a phenol adsorbent composition prior to contacting at least a portion of primarily para-xylene containing stream with a free radical.

5. The method of any of Clauses 1 to 4, further comprising contacting the para-xylene depleted stream with a xylene isomerization catalyst under conditions effective to isomerize xylenes in the para-xylene depleted stream and produce an isomerized stream.

6. The method of Clause 5, wherein contacting the para-xylene depleted stream with a xylene isomerization catalyst under conditions effective to isomerize xylenes includes contacting in the liquid phase and/or contacting in the vapor phase isomerization conditions.

7. The method of Clause 5, further comprising recycling at least part of the isomerized stream to the first separator.

8. The method of Clause 5, further comprising contacting the primarily para-xylene containing stream with a phenol adsorbent composition prior to contacting the para-xylene depleted stream with a xylene isomerization catalyst.

9. The method of any of Clauses 1 to 8 wherein the at least one catalyst composition comprises an alkylation catalyst and a phenol hydrogenation catalyst.

10. The method of any of Clauses 1 to 9, wherein the alkylation catalyst and the hydrogenation catalyst are the same.

11. The method of any of Clauses 1 to 10, wherein the alkylation catalyst is located in a first zone of the reactor proximate the reactor inlet and the hydrogenation catalyst is located in a second zone of the reactor proximate the reactor inlet.

12. The method of any of Clauses 1 to 11, wherein the reactor comprises first and second reactor beds, and the alkylation catalyst is located in a first reactor bed and the hydrogenation catalyst is located in a second reactor bed.

13. The method of any of Clauses 1 to 12, wherein passing an inert gas through the catalyst comprises passing nitrogen, argon, or a mixture thereof through the catalyst.

14. The method of any of Clauses 1 to 13, wherein passing a reducing agent through the catalyst comprises passing a composition comprising molecular hydrogen through the catalyst.

15. The method of any of Clauses 1 to 14, further comprising, prior to contacting at least part of a toluene-containing stream with an oxygenate, separating a feed stream comprising $C_{6+}$ aromatic hydrocarbons into at least the toluene-containing stream and a $C_8$ aromatic hydrocarbon-containing stream.

16. The method of any of Clauses 1 to 15, further comprising contacting the at least one para-xylene enriched stream with a phenol adsorbent composition upstream of the second separator.

17. The method of any of Clauses 1 to 16, further comprising contacting the at least one para-xylene-product stream with a phenol adsorbent composition upstream of the third separator.

18. The method of any of Clauses 1 to 17, wherein the oxygenate comprises methanol.

19. A hydrocarbon conversion apparatus comprising:

a) a reactor having therein one or more catalyst compositions effective to convert an aromatic hydrocarbon stream comprising ≥5.0 wt % toluene and/or benzene having phenol therein to a reactor effluent stream comprising para-xylene and having a lower concentration of phenol than the toluene-containing stream;

b) an inert gas source in fluid communication with the reactor and configured to provide an inert gas to the one or more catalyst compositions;

c) a reducing agent source configured to provide a reducing agent to the one or more catalyst compositions to reduce metal oxide content thereof;

d) a first separator for recovering para-xylene from the reactor effluent stream to produce at least one para-xylene-enriched stream; and e) a second separator configured to separate from the at least one para-xylene enriched stream at least one toluene-enriched stream and at least one para-xylene-product stream.

20. The apparatus of Clause 19, further comprising a third separator configured to separate a primarily para-xylene containing stream and a para-xylene depleted stream from the at least one para-xylene-product stream.

21. The method of Clause 20, further comprising an oxidation unit for contacting at least a portion of primarily para-xylene containing stream with a free radical under conditions effective to oxidize at least a portion of the para-xylene to produce an oxidized effluent having terephthalic acid therein and a recovery unit for recovering terephthalic acid from the oxidized effluent.

22. The method of Clause 20, further comprising a phenol adsorbing unit having a phenol-adsorbent composition therein for removing at least a portion of the phenol in the primarily para-xylene containing stream, the phenol adsorbing system located upstream of the oxidation unit.

23. The method of any of Clauses 19 to 22, further comprising a xylene isomerization unit having a xylene isomerization catalyst therein and operable to convert to isomerize xylenes in the para-xylene-depleted stream and produce an isomerized stream.

24. The method of Clause 23, wherein the xylene isomerization unit comprises a liquid-phase xylene isomerization unit and/or a vapor-phase xylene isomerization unit.

25. The method of Clause 23, further comprising recycling system for recycling at least part of the isomerized stream to the first separator.

26. The method of Clause 23, further comprising a phenol adsorption unit having a phenol-adsorbent composition therein for removing at least a portion of the phenol in the primarily para-xylene containing stream upstream of the xylene isomerization unit.

27. The method of any of Clauses 19 to 26, wherein the inert gas source comprises a source of nitrogen, argon, or a mixture thereof.

28. The method of Clauses 19 to 27, wherein the reducing agent source comprises a source of molecular hydrogen.

29. The method of Clauses 19 to 28, further comprising upstream of the reactor an initial separator for separating a feed stream comprising $C_{6+}$ aromatic hydrocarbons into at least the toluene-containing stream and a $C_8$ aromatic hydrocarbon-containing stream.

30. The method of Clauses 19 to 29, further comprising upstream of the second separator, a phenol adsorption unit having a phenol-adsorbent composition therein for removing at least a portion of the phenol from the at least one para-xylene enriched stream.

31. The method of Clauses 19 to 30, further comprising further comprising downstream of the second separator, a phenol adsorption unit having a phenol-adsorbent composition therein for removing at least a portion of the phenol from the at least one para-xylene-product stream.

32. The method of Clauses 19 to 31, wherein the oxygenate comprises methanol.

All documents described herein are incorporated by reference herein for purposes of all jurisdictions where such practice is allowed, including any priority documents and/or testing procedures to the extent they are not inconsistent with this text, provided however that any priority document not named in the initially filed application or filing documents is not incorporated by reference herein. As is apparent from the foregoing general description and the specific aspects, while forms of the disclosure have been illustrated and described, various modifications can be made without departing from the spirit and scope of the disclosure. Accordingly, it is not intended that the disclosure be limited thereby. Likewise, whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa. Aspects of the disclosure include those that are substantially free of or essentially free of any element, step, composition, ingredient or other claim element not expressly recited or described.

What is claimed is:

1. A hydrocarbon conversion, comprising:
a) contacting in at least a first reactor an inert gas with one or more catalyst compositions suitable for methylation of toluene and/or hydrogenation of phenol, wherein the one or more catalyst compositions comprise an alkylation catalyst and a phenol hydrogenation catalyst, and wherein the alkylation catalyst is located in a first zone of the first reactor proximate the reactor inlet and the hydrogenation catalyst is located in a second zone of the first reactor proximate the reactor inlet;
b) contacting a reducing agent with the one or more catalyst compositions under suitable conditions to reduce the metal oxide content of the one or more catalyst compositions;
c) contacting at least part of an aromatic hydrocarbon stream comprising ≥5.0 wt % toluene and/or benzene with a oxygenate in the presence of the alkylation catalyst and under conditions effective to convert toluene to xylenes and produce a reactor effluent stream comprising para-xylene and phenol;
d) contacting the reactor effluent stream with the hydrogenation catalyst to convert at least a portion of the phenol in the reactor effluent stream to cyclohexanone;
e) separating in a first separator at least one para-xylene-enriched stream from the reactor effluent stream; and
f) separating in a second separator from the at least one para-xylene enriched stream at least one toluene-enriched stream and at least one para-xylene-product stream.

2. The method of claim 1, further comprising separating in a third separator a primarily para-xylene containing stream and para-xylene depleted stream from the at least one para-xylene-product stream.

3. The method of claim 2, further comprising
g) contacting at least a portion of primarily para-xylene containing stream with a free radical under conditions effective to oxidize at least a portion of the para-xylene to produce an oxidized effluent having terephthalic acid therein;
h) recovering terephthalic acid from the oxidized effluent.

4. The method of claim 3, further comprising contacting the primarily para-xylene containing stream with a phenol adsorbent composition prior to contacting the at least a portion of the primarily para-xylene containing stream with the free radical.

5. The method of claim 2, further comprising contacting the para-xylene depleted stream with a xylene isomerization catalyst under conditions effective to isomerize xylenes in the para-xylene depleted stream and produce an isomerized stream.

6. The method of claim 5, wherein contacting the para-xylene depleted stream with a xylene isomerization catalyst under conditions effective to isomerize xylenes includes contacting in the liquid phase and/or contacting in the vapor phase isomerization conditions.

7. The method of claim 5, further comprising recycling at least part of the isomerized stream to the first separator.

8. The method of claim 5, further comprising contacting the primarily para-xylene containing stream with a phenol adsorbent composition prior to contacting the para-xylene depleted stream with a xylene isomerization catalyst.

9. The method of claim 1, wherein passing an inert gas through the one or more catalyst compositions comprises passing nitrogen, argon, or a mixture thereof through the one or more catalyst compositions.

10. The method of claim 1, wherein passing a reducing agent through the one or more catalyst compositions comprises passing a composition comprising molecular hydrogen through the one or more catalyst compositions.

11. The method of claim 1, further comprising, prior to contacting at least part of a toluene-containing stream with the oxygenate, separating a feed stream comprising $C_{6+}$ aromatic hydrocarbons into at least the toluene-containing stream and a $C_8$ aromatic hydrocarbon-containing stream.

12. The method of claim 1, further comprising at least one of:
  contacting the at least one para-xylene enriched stream with a phenol adsorbent composition upstream of the second separator; and
  contacting the at least one para-xylene-product stream with a phenol adsorbent composition upstream of the third separator.

13. The method of claim 1, wherein the oxygenate comprises methanol.

14. A hydrocarbon conversion, comprising:
  a) contacting in at least a first reactor an inert gas with one or more catalyst compositions suitable for methylation of toluene and hydrogenation of phenol, wherein the one or more catalyst compositions comprise an alkylation catalyst and a phenol hydrogenation catalyst, and wherein the first reactor comprises first and second reactor beds, and the alkylation catalyst is located in a first reactor bed and the hydrogenation catalyst is located in a second reactor bed;
  b) contacting a reducing agent with the one or more catalyst compositions under suitable conditions to reduce the metal oxide content of the first catalyst composition;
  c) contacting at least part of an aromatic hydrocarbon stream comprising ≥5.0 wt % toluene and/or benzene with a oxygenate in the presence of the alkylation catalyst and under conditions effective to convert toluene to xylenes and produce a reactor effluent stream comprising para-xylene and phenol;
  d) contacting the reactor effluent stream with the hydrogenation catalyst to convert at least a portion of the phenol in the reactor effluent stream to cyclohexanone;
  e) separating in a first separator at least one para-xylene-enriched stream from the reactor effluent stream; and
  f) separating in a second separator from the at least one para-xylene enriched stream at least one toluene-enriched stream and at least one para-xylene-product stream.

15. The method of claim 14, further comprising separating in a third separator a primarily para-xylene containing stream and para-xylene depleted stream from the at least one para-xylene-product stream.

16. The method of claim 15, further comprising:
  g) contacting at least a portion of primarily para-xylene containing stream with a free radical under conditions effective to oxidize at least a portion of the para-xylene to produce an oxidized effluent having terephthalic acid therein;
  h) recovering terephthalic acid from the oxidized effluent; and
  i) contacting the primarily para-xylene containing stream with a phenol adsorbent composition prior to contacting the at least a portion of the primarily para-xylene containing stream with the free radical.

17. The method of claim 15, further comprising at least one of:
  j) contacting the para-xylene depleted stream with a xylene isomerization catalyst under conditions effective to isomerize xylenes in the para-xylene depleted stream and produce an isomerized stream; and
  k) recycling at least part of the isomerized stream to the first separator.

18. The method of claim 17, further comprising contacting the primarily para-xylene containing stream with a phenol adsorbent composition prior to contacting the para-xylene depleted stream with a xylene isomerization catalyst.

19. The method of claim 14, wherein passing an inert gas through the one or more catalyst compositions and the dehydrogenation catalyst comprises passing nitrogen, argon, or a mixture thereof through the one or more catalyst compositions.

20. The method of claim 14, wherein passing a reducing agent through the one or more catalyst compositions comprises passing a composition comprising molecular hydrogen through the one or more catalyst compositions.

21. The method of claim 15, further comprising contacting the primarily para-xylene containing stream with a phenol adsorbent composition prior to contacting the para-xylene depleted stream with a xylene isomerization catalyst.

22. The method of claim 14, further comprising, prior to contacting at least part of a toluene-containing stream with the oxygenate, separating a feed stream comprising $C_{6+}$ aromatic hydrocarbons into at least the toluene-containing stream and a $C_8$ aromatic hydrocarbon-containing stream.

23. The method of claim 14, further comprising at least one of:
  contacting the at least one para-xylene enriched stream with a phenol adsorbent composition upstream of the second separator; and
  contacting the at least one para-xylene-product stream with a phenol adsorbent composition upstream of the third separator.

24. A hydrocarbon conversion, comprising:
  a) contacting in at least a first reactor an inert gas with one or more catalyst compositions suitable for methylation of toluene and hydrogenation of phenol, wherein the one or more catalyst compositions comprise an alkylation catalyst and a phenol hydrogenation catalyst, and wherein the alkylation catalyst and the hydrogenation catalyst are the same;
  b) contacting a reducing agent with the one or more catalyst compositions under suitable conditions to reduce the metal oxide content of the first catalyst composition;
  c) contacting at least part of an aromatic hydrocarbon stream comprising ≥5.0 wt % toluene and/or benzene with a oxygenate in the presence of the one or more catalyst compositions and under conditions effective to convert toluene to xylenes and produce para-xylene and phenol and to convert at least a portion of the phenol to cyclohexanone;
  d) producing a reactor effluent stream from the first reactor;
  e) separating in a first separator at least one para-xylene-enriched stream from the reactor effluent stream; and
  f) separating in a second separator from the at least one para-xylene enriched stream at least one toluene-enriched stream and at least one para-xylene-product stream.

25. The method of claim 24, further comprising separating in a third separator a primarily para-xylene containing stream and para-xylene depleted stream from the at least one para-xylene-product stream.

26. The method of claim 25, further comprising
  g) contacting at least a portion of primarily para-xylene containing stream with a free radical under conditions effective to oxidize at least a portion of the para-xylene to produce an oxidized effluent having terephthalic acid therein;
  h) recovering terephthalic acid from the oxidized effluent; and
  i) contacting the primarily para-xylene containing stream with a phenol adsorbent composition prior to contacting at least a portion of primarily para-xylene containing stream with a free radical.

27. The method of claim 25, further comprising at least one of:
j) contacting the para-xylene depleted stream with a xylene isomerization catalyst under conditions effective to isomerize xylenes in the para-xylene depleted stream and produce an isomerized stream; and
k) recycling at least part of the isomerized stream to the first separator.

28. The method of claim 27, further comprising contacting the primarily para-xylene containing stream with a phenol adsorbent composition prior to contacting the para-xylene depleted stream with a xylene isomerization catalyst.

29. The method of claim 24, wherein passing an inert gas through the one or more catalyst compositions comprises passing nitrogen, argon, or a mixture thereof through the one or more catalyst compositions.

30. The method of claim 24, wherein passing a reducing agent through the one or more catalyst compositions comprises passing a composition comprising molecular hydrogen through the one or more catalyst compositions.

31. The method of claim 25, further comprising at least one of:
contacting the primarily para-xylene containing stream with a phenol adsorbent composition prior to contacting the para-xylene depleted stream with a xylene isomerization catalyst; and
prior to contacting at least part of a toluene-containing stream with an oxygenate, separating a feed stream comprising $C_{6+}$ aromatic hydrocarbons into at least the toluene-containing stream and a $C_8$ aromatic hydrocarbon-containing stream.

32. The method of claim 24, further comprising at least one of:
contacting the at least one para-xylene enriched stream with a phenol adsorbent composition upstream of the second separator; and
contacting the at least one para-xylene-product stream with a phenol adsorbent composition upstream of the third separator.

* * * * *